United States Patent [19]
Goldreyer

[11] Patent Number: 5,391,194
[45] Date of Patent: Feb. 21, 1995

[54] APPARATUS FOR USE IN PROGRAMMING CARDIAC PACEMAKERS AND METHOD OF USING THE SAME

[75] Inventor: Bruce N. Goldreyer, Rancho Palos Verdes, Calif.

[73] Assignee: Pressure Products Medical Supplies, Inc., Rancho Palos Verdes, Calif.

[21] Appl. No.: 10,047

[22] Filed: Jan. 28, 1993

[51] Int. Cl.[6] .......................................... A61N 1/372
[52] U.S. Cl. ..................................................... 607/31
[58] Field of Search ..................... 607/1, 2, 31, 32, 30, 607/60

[56] References Cited

U.S. PATENT DOCUMENTS

| | | | |
|---|---|---|---|
| 4,550,731 | 11/1985 | Batina et al. | 607/31 |
| 4,865,039 | 9/1989 | Dunseath, Jr. | 128/640 |
| 5,085,217 | 2/1992 | Shimizu | 128/640 |

*Primary Examiner*—William E. Kamm
*Assistant Examiner*—Kennedy J. Schaetzle
*Attorney, Agent, or Firm*—Beehler & Pavitt; Daniel L. Dawes

[57] ABSTRACT

Reprogramming of implanted pacemakers is made more reliable and secure by utilizing a pad having an adhesive surface provided on its upper and lower contacting layers. In the illustrated embodiment, the pad is generally circular with a central circular hole. The pad is placed over the implanted pacemaker at a predetermined position utilizing the central aperture hole for alignment of the pad on the site of pacemaker implantation. An auxiliary cardiac device, such as a programming head, is then disposed on the upper adhesive of the circular pad. The shape of the pad inherently induces the medical technician to appropriately register the auxiliary device relative to the pacemaker. The double adhesive layers of the pad provide temporary affixation of the auxiliary device relative to the pacemaker during the reprogramming or other pacemaker manipulation so that inadvertent relative movement of the auxiliary device relative to the programmable pacemaker is avoided.

14 Claims, 1 Drawing Sheet

APPARATUS FOR USE IN PROGRAMMING CARDIAC PACEMAKERS AND METHOD OF USING THE SAME

BACKGROUND OF THE INVENTION

1. Field of the Invention

The invention relates to the field of programmable pacemakers and in particular to devices used to reprogram cardiac pacemakers.

2. Description of the Prior Art

Many cardiac patients can enjoy healthier lives and longer life spans by artificially pacing their hearts. A pacemaker is subcutaneously implanted above the chest wall and a cardiac catheter or catheters are then led through a vein into the heart to implant or dispose a pacemaking tip in a predetermined position within the heart. The pacemaker then delivers a timed stimulating pulse to ensure that a regular heart rhythm is maintained. Early pacemakers had a fixed protocol or rhythm of stimulating pulses which they delivered to the heart. The sophistication of the pacemaker circuitry increased to provide different types of demand pacemakers which would provide a stimulating pulse only upon certain conditions or to alter the stimulating pulse depending upon the heart rates or other biophysical parameters such as respiration or activity.

The sophistication and flexibility of pacemakers has continued to rapidly expand to the point where pacemakers which are now implanted are typically reprogrammable, that is any one of a variety of cardiac pacing protocols can be programmed into the pacemaker even after it is subcutaneously implanted. The pacemaker thus becomes generally programmable and the cardiac pacing can be diagnostically changed as the patient's diagnosis changes or as his cardiac disease state improves or deteriorates.

Typically, the pacemaker is programmed by placing a radio frequency transmitter or programming head over the pacemaker, sometimes over a predetermined portion of the pacemaker such as the upper one-third. Various testing procedures are practiced to determine if the programming head is properly positioned relative to the pacemaker pulse generator. When programming is performed, it is important not to alter or reposition the programming head above the pacemaker. Such repositioning might cause failure of correct program transmission or incomplete programming.

In addition, any movement of the programming probe while positioned over the pacemaker may interfere with proper decoding of the telemetry signal received from the pacemaker. This in turn may result in the display of inaccurate pacemaker data transmission. Typically, programming of the pacemaker may require the retention of the programming head over the pacemaker for time period ranging from 5 to 25 seconds repetitively over 10 to 30 minutes. In most cases, the programming head is simply hand held over the pacemaker for this time period. In most case, the technician is able to adequately maintain the programming head in a fixed or still position relative to the pacemaker. However, the number of instances in which movement of the programming head relative to the pacemaker does occur and the consequences of a deleterious effect either on the pacemaker, the patient, or both of such movement is great enough as to require additional security measures to be undertaken to ensure successful pacemaker manipulation. This is particularly the case when programming in the upright position or during exercise.

Therefore, what is needed is some type of means which may be used in connection with programmable pacemakers for positioning a device, such as a programming head over a predetermined position on the embedded pacemaker for a predetermined time without substantial risk of inadvertent relative movement between the two.

BRIEF SUMMARY OF THE INVENTION

The invention is an apparatus for use in programming an implanted pacemaker comprising a double sided adhesive pad for providing a fixation at a skin implantation site over the implanted pacemaker and for providing a fixation to an auxiliary device used in programming the implanted pacemaker. As a result, the pacemaker may be reliably manipulated without risk of relative movement of the auxiliary device with respect to the pacemaker during manipulation of the pacemaker.

The pad comprises an element for centering the pad at a predetermined location relative to the implanted pacemaker. The element for registering the pad comprises a central aperture defined through the pad.

The pad also comprises an element for registering the auxiliary device with respect the pad. The element for registering the auxiliary device comprises a shape defining the pad to simulate the shape its auxiliary device. The auxiliary device is positioned on the pad so that the simulating shape of the pad tends to match that of the auxiliary device.

The pad has two opposing generally flat surfaces. The surfaces are provided with a sticky adhesive layers and further comprise a pair of protective covers temporarily affixed to the opposing surfaces of the pad bearing the adhesive layers. The pair of protective covers maintain the adhesive layers free and operative for use and facilitate handling of the pad prior to affixation to the to the site and auxiliary device.

In the illustrated embodiment the pad is generally circular and has a central aperture defined therethrough and is comprised of closed cell foam bearing an adhesive layer on opposing surfaces thereof.

The invention is also characterized as a method for manipulating an auxiliary device relative to an implanted programmable pacemaker comprising the steps of positioning an adhesive pad on the implantation site of the pacemaker at a predetermined position relative to the pacemaker. The pad is adhered to the implantation site at the predetermined position. The auxiliary device is positioned on the pad at a predetermined position relative to the pad. The auxiliary device is then adhered to the pad at the predetermined position on the pad. As a result, the auxiliary device is temporarily affixed relative to a predetermined position of the pacemaker during manipulation of the pacemaker.

The steps of positioning and adhering the pad to the implantation site are performed simultaneously by providing an adhesive layer on the pad and disposing the adhesive layer in contact with the implantation site. Similarly, the steps of positioning and adhering the auxiliary device are performed simultaneously and comprise the step of disposing the auxiliary device on an adhesive bearing layer of the pad at a predetermined position on the pad.

The step of positioning the pad relative to the implantation site comprises the step of positioning a guiding aperture defined in the pad at the predetermined position relative to the implantation site. The step of positioning the auxiliary device relative to the pad comprises the step of registering the auxiliary device to the pad by conforming the configuration of the auxiliary device with a similar shape provided by the pad.

The invention now having been summarized, it may be better visualized by turning to the following drawings where like elements are referenced by like numerals.

The invention and its various embodiments may be better understood by now turning to the following detailed description.

DETAILED DESCRIPTION OF THE PREFERRED EMBODIMENTS

Reprogramming of implanted pacemakers is made more reliable and secure by utilizing a pad having an adhesive surface provided on its upper and lower contacting layers. In the illustrated embodiment, the pad is generally circular with a central circular hole. The pad is placed over the implanted pacemaker at a predetermined position utilizing the central aperture hole for alignment of the pad on the site of pacemaker implantation. An auxiliary cardiac device, such as a programming head, is then disposed on the upper adhesive of the circular pad. The shape of the pad inherently induces the medical technician to appropriately register the auxiliary device relative to the pacemaker. The double adhesive layers of the pad provide temporary affixation of the auxiliary device relative to the pacemaker during the reprogramming or other pacemaker manipulation so that inadvertent relative movement of the auxiliary device relative to the programmable pacemaker is avoided.

Figure 1:
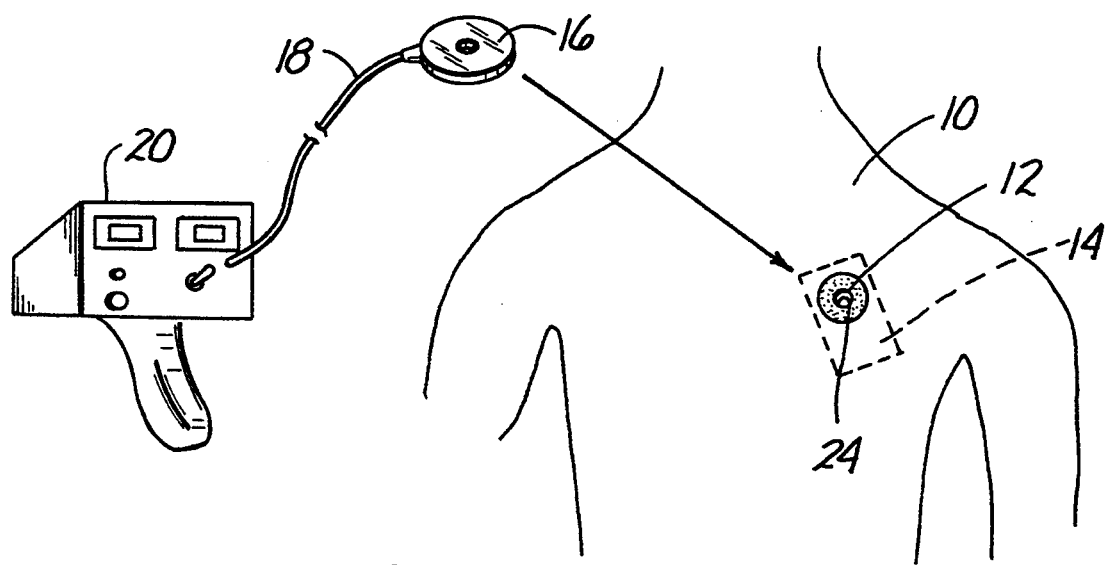
FIG. 1 is a diagrammatic depiction of the invention as applied to a patient and used in combination with a programming head.

FIG. 1 is a diagrammatic depiction of a patient 10 to which the adhesive fixture 12 of the invention has been applied. Pad 12 is placed on patient 10 over a subcutaneously planted pacemaker 14. It is contemplated that pad 12 will be specifically positioned with respect to pacemaker 14 so as to assume a predetermined locational relationship with respect to it. In other words, pad 12 must be positioned over a selected portion, such as the upper third or some other portion wherein programmability or recharging or other pacemaker manipulation is preferably performed relative to pacemaker 14.

In the illustrated embodiment of FIG. 1, a programming head 16 connected by cable 18 to a conventional charging apparatus 20 is depicted as being placed over pad 12 in pacemaker 14. Pad 12 therefore serves the function of providing an easily visible target and means for registration to which programming head 16 or other some other device such as a magnet may be conveniently and reliably positioned or registered.

Figure 2:
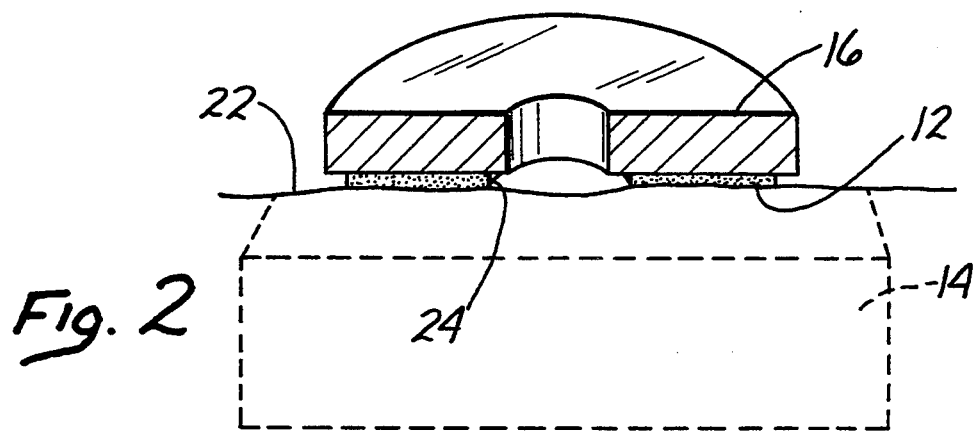
FIG. 2 is a cross sectional view in enlarged scale showing the invention used in combination with the programming head and placed in position above a subcutaneously planted pacemaker.

The cross sectional view of FIG. 2 in enlarged scale provides an illustrative example of the final positioning of programming head 16 or such other pacemaker device onto pad 12 over pacemaker 14, which has been subcutaneously implanted beneath skin surface 22.

Pad 12 in the illustrated embodiment is a circle having a circular central opening 24 defined therein. Opening 24 provides accessibility to the underlying site of pacemaker 14 in addition to providing a shape which allows pad 12 to be easily centered or registered relative to pacemaker 14. This allows the medical technician to visually and easily register or position magnetic charging head 16 onto pad 12.

In the illustrated embodiment it is seen that pad 12 has shape generally similar in configuration to the device which is attached to it, namely programming head 16. Therefore, it is contemplated that pad 12 may be provided with other geometric configurations that are appropriately adapted to other devices, such as other types of programming heads, which because of their shape allow if not psychologically compel the user to properly align the auxiliary pacemaking apparatus onto pad 12 and hence appropriately position the auxiliary apparatus relative to pacemaker 14.

Figure 3:
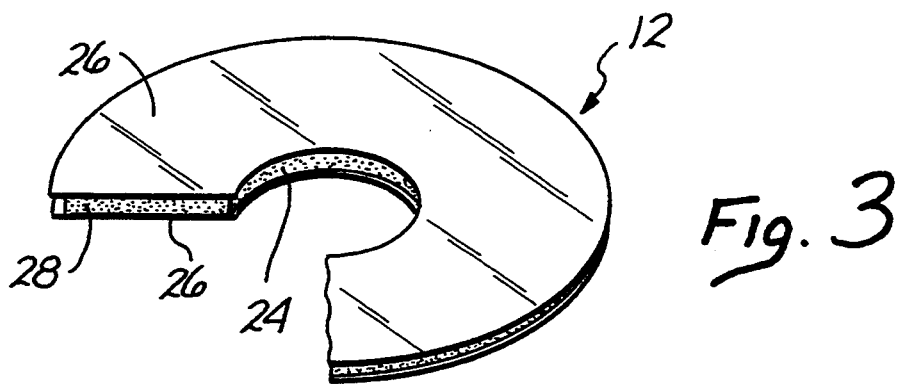
FIG. 3 is a partially cut away perspective view in enlarged scale of the invention shown in isolation in its preapplication configuration.

FIG. 3 is perspective view of a partially cut away embodiment of pad 12 shown in its preapplication configuration. Prior to being applied to skin surface 22, pad 12 is provided with an upper and lower protective disk 26 which adheres to the upper and lower surfaces of pad 12 through a sticky, reusable adhesive. Pad 12 is thus comprised of a closed cell form core 28 fabricated in the illustrated embodiment as a highly flattened disc or toroid with central aperture 24. When in use protective disks 26 of peel-away paper are removed from upper or lower surfaces of pad 12, which is then placed by the medical technician over the appropriate location on skin surface 22 above pacemaker 14. The upper disk 26 is removed, if it has not already done so, thereby providing an open sticky surface available for adhesion to the auxiliary medical apparatus, such as programming head 16 in FIG. 1. Thereafter, the adhesion of pad 12 is sufficient to retain the auxiliary apparatus, such as magnet 16, firmly adhered to pad 12. Pad 12 is then appropriately retained in position on skin surface 22 over pacemaker 14 during the entire pacemaker procedure. There is virtually no risk of inadvertent movement of the auxiliary apparatus relative to the pacemaker during the procedure either as a result of patient movement or inadvertent movement by the medical technician.

Therefore, what has been described is an expensive and simple, but very effective device to assist in the use of auxiliary cardiac apparatus for manipulating and performing in operations with respect to implanted programmable pacemakers. In addition to providing the essential function of relative fixation, pad 12 of the invention also provides a simple and highly effective means of providing registration to the both the implanted pacemaker and to the applied auxiliary cardiac equipment. The nature of the pad is such that it naturally induces the operator to make the appropriate registrations even in the absence of detailed registration instructions or training, since pad 12 has a structure with an evident center and an overall shape which simulates the auxiliary device and encourages appropriate registration with respect to the auxiliary device.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptionally equivalent, and also what essentially incorporates the germ of the invention.

I claim:

1. An apparatus for use in programming an implanted pacemaker comprising:
   a double sided adhesive pad for fixing on a first side of said pad to a skin implantation site over said implanted pacemaker and for fixing on a second side to an auxiliary device used in programming said implanted pacemaker;
   means for visually registering said pad relative to said implanted pacemaker as said pad is being fixed to said skin implantation site; and
   means for visually registering said auxiliary device relative to said pad,
   whereby said pacemaker may be reliably programmed without risk of relative movement of said auxiliary device with respect to said pacemaker during programming of said pacemaker.

2. The apparatus of claim 1 wherein said means for registering said pad comprises a central aperture defined completely through said pad to permit visual sighting and alignment of said pad as said pad is disposed onto said implantation site.

3. A method for manipulating an auxiliary device relative to an implanted programmable pacemaker comprising the steps of:
   positioning an adhesive pad on the implantation site of said pacemaker at a predetermined position relative to said pacemaker;
   adhering said pad to said implantation site at said predetermined position;
   positioning said auxiliary device on said pad at a predetermined position relative to said pad; and
   adhering said auxiliary device to said pad at said predetermined position on said pad,
   whereby said auxiliary device is temporarily affixed relative to a predetermined position of said pacemaker during manipulation of said pacemaker.

4. The method of claim 3 wherein said steps of positioning and adhering said pad to said implantation site are performed simultaneously by providing an adhesive layer on said pad and disposing said adhesive layer in contact with said implantation site.

5. The method of claim 3 wherein said steps of positioning and adhering said auxiliary device are performed simultaneously and comprise the step of disposing said auxiliary device on an adhesive bearing layer of said pad at a predetermined position on said pad.

6. The method of claim 5 wherein said steps of positioning and adhering said pad to said implantation site are performed simultaneously by providing an adhesive layer on said pad and disposing said adhesive layer in contact with said implantation site.

7. The method of claim 3 wherein said step of positioning said pad relative to said implantation site comprises the step of positioning a guiding aperture defined in said pad at said predetermined position relative to said implantation site.

8. The method of claim 3 wherein said step of positioning said auxiliary device relative to said pad comprises the step of registering said auxiliary device to said pad by conforming the configuration of said auxiliary device with a similar shape provided by said pad.

9. The method of claim 8 wherein said step of positioning said pad relative to said implantation site comprises the step of positioning a guiding aperture defined in said pad at said predetermined position relative to said implantation site.

10. A method of registering an auxiliary device to a reprogrammable implanted pacemaker and temporarily maintaining an auxiliary device in position with respect to said pacemaker comprising the steps of:
    exposing an adhesive layer on a first surface of a shaped foam pad having an alignment aperture defined therethrough;
    viewing said implantation site over said pacemaker by using said alignment aperture to register said pad relative to said implanted pacemaker; and
    then simultaneously disposing said adhesive first surface on a predetermined site over said implanted pacemaker, said alignment aperture provided for viewing said implantation site over said pacemaker as said pad is disposed over said implanted pacemaker.

11. The method of claim 10 further comprising the step of exposing an upper adhesive layer of said pad and disposing said auxiliary device on said upper exposed surface of said pad to temporarily affix said auxiliary device to said pad and hence relative to said implanted pacemaker.

12. The method of claim 11 wherein said step of disposing comprises the step of registering said auxiliary device with respect to said pad by aligning said auxiliary device with respect to a predetermined shape of said pad.

13. The method of claim 12 wherein said predetermined shape of said pad simulates the shape of the contacting surface of said auxiliary device when disposed above said implanted pacemaker.

14. The method of claim 12 wherein said pad is generally circular and has a central circular aperture defined therethrough, to simulate a circulate target symbol.

* * * * *